US006566369B2

(12) United States Patent
Cautreels et al.

(10) Patent No.: US 6,566,369 B2
(45) Date of Patent: May 20, 2003

(54) MEDICAMENT CONTAINING CILANSETRON FOR THE TREATMENT OF NON-OBSTIPATIVE MALE IRRITABLE BOWEL SYNDROME PATIENTS

(75) Inventors: Werner L. M. Cautreels, Weesp (NL); Claus Rudolf Steinborn, Seelze (DE); Heinz Guenter Krause, Burgdorf (DE); Steven David Caras, Marietta, GA (US); Egbertus Hendrikus Evert Biesheuvel, Weesp (NL); Albertus Hermannus Dirk Plekkenpol, Hilversum (NL)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 09/908,735

(22) Filed: Jul. 20, 2001

(65) Prior Publication Data

US 2002/0040033 A1 Apr. 4, 2002

Related U.S. Application Data

(60) Provisional application No. 60/220,848, filed on Jul. 26, 2000.

(30) Foreign Application Priority Data

Jul. 26, 2000 (DE) ......................................... 100 36 645
May 14, 2001 (DE) ......................................... 101 23 447

(51) Int. Cl.[7] ............................................. A61K 31/437
(52) U.S. Cl. .................... 514/292; 514/183; 514/230.5; 514/254.06; 514/284; 514/304; 514/305; 514/306; 514/394; 514/397
(58) Field of Search .................. 514/292, 885, 514/183, 230.5, 254.06, 284, 304, 305, 306, 394, 397

(56) References Cited

FOREIGN PATENT DOCUMENTS

| WO | 99/17755 | 4/1999 |
|---|---|---|
| WO | WO9917755 | 4/1999 |
| WO | 01/45685 | 6/2001 |

OTHER PUBLICATIONS

C. Beglinger, et al., "Effect of Cilansetron, A Specific 5–HT3 Receptor Antagonist, on Gastrointestinal Motor Function in Normal Subjects" Development of Gastroenterology, Department of Internal Medicine, University Clinic Basel Petersgraben, Article No. XP–001058426 (1996).

W.G. Thompson, et al, "Irritable Bowel Syndrome: Guidelines for the Diagnosis" Gastroenterology International, vol. 2, No. 2, 1989.

W.G. Thompson, et al, "Functional bowel disorders and functional abdominal pain" Gut, vol. 45, 1999.

W.G. Thompson, "Irritable bowel syndrome: pathogenesis and management" The Lancet, vol. 341, Jun. 19, 1993.

"Irritable bowel syndrome—Cilansetron" Manufacturing Chemist, 2000.

A. Botella, et al., "Intracolonic glycerol induces abdominal contractions in rats: role of 5–HT3 receptors" Fundam. Clin. Pharmacol, 1998.

X. Rabasseda, et al., "Cilansetron" Drugs Future, 1999.

George Stacher, et al., "Effects of the 5–HT3 antagonist cilansetron vs placebo on phasic sigmoid colonic motility in healthy man: a double–blind crossover trial" Br. J. Clin. Pharmacol, 2000.

Copy of Search Report (2002).

*Primary Examiner*—Frederick Krass
(74) *Attorney, Agent, or Firm*—Crowell & Moring LLP

(57) ABSTRACT

The present invention relates to the use of cilansetron for the treatment of non-obstipative male IBS patients.

3 Claims, No Drawings

MEDICAMENT CONTAINING CILANSETRON FOR THE TREATMENT OF NON-OBSTIPATIVE MALE IRRITABLE BOWEL SYNDROME PATIENTS

CROSS REFERENCE TO RELATED APPLICATIONS

This application claims priority of U.S. Provisional Patent Application No. 60/220,848, filed Jul. 26, 2000. Convention priority is also claimed based on Federal Republic of Germany Patent Application Nos. DE 100 36 645.7, filed Jul. 26, 2001 and DE 101 23 447.3, filed May 14, 2001.

BACKGROUND OF THE INVENTION

The present invention relates to a novel medicinal use of cilansetron or the acid addition salts thereof.

Cilansetron is a $5HT_3$-receptor antagonist which falls within the scope of European Patent No. EP 297,651 B1 and has the chemical name (R)-(−)-4,5,6,8,9,10-hexahydro-10-[(2-methyl-1H-imidazol-1-yl)methyl]-11H-pyrido-[3,2,1-jk]-carbazol-11-one.

The use of, inter alia, cilansetron for the production of pharmaceutical preparations for the treatment of functional disturbances in the lower intestinal tract in larger mammals and humans which involve increased sensitivity to pain and/or abnormally accelerated stool passage in the colon region is already known from European Patent No. EP 601,345 B1. The functional disturbances which can be treated, inter alia, by cilansetron also include, for example, "irritable bowel syndrome" (=IBS), in particular in conjunction with abnormally accelerated passage of the stool through the colon.

In International Patent Application Publication No. WO 99/17755, $5HT_3$-receptor antagonists are described which are particularly well-suited for the treatment of non-obstipative (=diarrhea-predominant IBS patient group; in contrast to the obstipation-predominant IBS patient group) female IBS patients. Alosetron is cited as an example in WO 99/17755. In clinical tests, alosetron exhibited significantly better effectiveness on female IBS patients, compared with the effectiveness on male IBS patients. On male test subjects treated with alosetron, no significant improvement in condition compared with the placebo group was noted in these clinical tests. In one embodiment of said application no. WO 99/17755, cilansetron also is mentioned among other substances as coming within the scope of the disclosure.

SUMMARY OF THE INVENTION

It has now surprisingly been discovered that cilansetron is equally suitable for the treatment of non-obstipative male and female patients suffering from irritable bowel syndrome (=IBS).

The invention therefore relates to the use of cilansetron or the pharmacologically acceptable acid addition salts and/or solvates thereof for the production of pharmaceutical preparations for the treatment and/or prophylaxis of irritable bowel syndrome (=IBS) in non-obstipative male patients.

IBS designates a group of symptoms, accompanied by pain and/or a feeling of unwellness in the lower abdomen and altered intestinal activity, such as diarrhea, obstipation (=constipation), or alternately diarrhea and obstipation. Since it has hitherto not been possible to give any clearly tangible physiological or other organic results as a cause of IBS, medical diagnosis of this illness is usually based on the absence or presence of a number of symptoms, which are generally regarded as typical of IBS and are recorded for example in the "Rome Criteria" (cf. W. G. Thompson et al., Gastroent. Int. 2 (1989) 92–95; W. G. Thompson et al., Gut 45/II (1999) II43–II 47; W. G. Thompson, Lancet 341 (1993) 1569–1572).

According to the invention, cilansetron may preferably be used in the form of cilansetron hydrochloride. Usually, cilansetron hydrochloride monohydrate is used. Further pharmacologically acceptable acid addition salts of cilansetron are known from EP 0 297 651 21.

Clinical test data prove the surprising suitability of cilansetron for the treatment of non-obstipative IBS patients of both the male and the female sex.

The effect of cilansetron on non-obstipative IBS patients of both sexes was investigated in a 12-week placebo-controlled clinical double-blind study with randomized selection and parallel test groups. Within the scope of the study, those IBS patients were regarded as non-obstipative patients whose symptoms met the "Rome Criteria" (see above) and the nature and frequency of whose stools met the following criteria:

i) $\leq 25\%$ IBS events adversely affected by obstipation.
ii) Characterised as non-obstipative in accordance with the "hRome Criteria" (see above, people who did not have <3 bowel movements per week and/or whose stools were not hard/lumpy in nature).
iii) $\leq 4$ days (in succession or not in succession) without bowel movement over a two-week observation period (="run-in period").
iv) Average nature of stools $\geq 4$ (corresponding to the "Bristol stool scale") over a two-week observation period.

Likewise, those patients were included in the study who responded "No" to the question about pain/feeling of unwellness in the lower abdomen only in $\leq 50\%$ of the cases or who judged their pain/feeling of unwellness in the lower abdomen as "restrictive" for<2 times over a two-week observation period.

Cilansetron was used in doses of 1, 2, 8 and 16 mg. The patients were checked weekly for "adequate alleviation" (=primary effectiveness parameter) of their IBS symptoms (stomach pains such as pains in the abdomen, abnormal bowel activity). Stomach pains such as pains in the abdomen, nature of the stools and stool frequency were rated daily by the patients (=secondary effectiveness parameter).

In a provisional result of the double-blind study, the data of a total of 454 patients (297 female patients and 157 male patients) were evaluated and plotted in the table below. Corresponding to the criteria on which the clinical double-blind study was based, in both patient subgroups of male IBS patients and female IBS patients the success rates relating to the "adequate alleviation" of the IBS symptoms as set forth in the table below were noted:

TABLE

| Success rate [%] | Placebo | Cilansetron (mg TID) | | | |
| --- | --- | --- | --- | --- | --- |
| | | 1 | 2 | 8 | 16 |
| Male patients | 30.0 | 51.3 | 63.0 | 56.3 | 58.6 |
| Female patients | 41.8 | 69.6 | 60.3 | 56.9 | 61.4 |

The "primary effectiveness parameter" corresponds to the success rate (="responder rate") to the question, which was put weekly to the patients, as to whether they had experienced "adequate alleviation" of their IBS symptoms (pain/ feeling of unwellness in the lower abdomen, abnormal bowel activity) during the course of the previous week. A "responder" is regarded as a patient who was treated for at least four weeks and who responded "Yes" to the question posed of whether "adequate alleviation" of his/her IIS symptoms had occurred for at least half of his/her treatment period.

At the end of the double-blind study, the data of a total of 471 patients (308 female patients and 163 male patients) were evaluated. The final success rates were 40% for the placebo group, 62% for the dose 1 mg cilansetron (TID), 53% for the dose 2 mg cilansetron (TID), 55% for the dose 8 mg cilansetron (TID) and 63% for the dose 16 mg cilansetron (TID). The success rates were very similar for the male and female patient groups. The greatest differences were observed for the dose of 1 mg cilansetron (TID).

It can be seen from the data given above that the non-obstipative IBS patients of both sexes respond to the treatment with cilansetron in all the dosages investigated.

It is particularly surprising that cilansetron is effective, as proved by the above results of the investigations, in the treatment of non-obstipative (=diarrhea-predominant) male IBS patients, since the person skilled in the art had to conclude from the contents of WO 99/17755 that cilansetron, just like alosetron, was preferentially suited only for the treatment of non-obstipative female IBS patients.

Previously-known $5HT_3$-receptor antagonists are usually administered twice a day for treatment of IBS (="BID dosage"). However, it has proved more advantageous for treating IBS patients of both sexes instead to administer $5HT_3$-receptor antagonists three times a day (="TID dosage"), for example in doses of 1 mg to 16 mg each time to IBS patients of both sexes. It is particularly preferred to spread the thrice daily administration of $5HT_3$-antagonists across the day and in particular to prescribe them after main meals (morning, mid-day and evening). Examples of $5HT_3$-receptor antagonists which can be more advantageously administered in three daily doses include alosetron, azasetron, dolasetron, granisetron, indisetron, itasetron, lerisetron, ondansetron, ramosetron, tropisetron and (R)-Zacopride. It has proved particularly advantageous for treating IBS patients of both sexes to administer cilansetron or the pharmacologically acceptable acid addition salts and/or solvates thereof to the patients three times a day, for example each time in doses of between 1 mg and 16 mg per administered dose.

In accordance with the invention, cilansetron or a pharmacologically acceptable acid addition salt of cilansetron may be contained as a therapeutic agent, together with conventional pharmaceutical auxiliaries and/or carriers, in solid or liquid pharmaceutical preparations. Examples of solid preparations are preparations which can be administered orally, such as tablets, coated tablets, capsules, powders or granules, or alternatively suppositories. These preparations may contain conventional pharmaceutical inorganic and/or organic carriers, such as talcum, lactose or starch, in addition to conventional pharmaceutical auxiliaries, for example lubricants or tablet disintegrating agents. Liquid preparations such as suspensions or emulsions of cilansetron may contain the usual diluents such as water, oils and/or suspension agents such as polyethylene glycols and the like. Other auxiliaries may additionally be added, such as preservatives, taste correctives and the like.

Cilansetron or a pharmacologically acceptable acid addition salt of cilansetron can be mixed and formulated with the pharmaceutical auxiliaries and/or carriers in a known manner. For the production of solid medicament forms, cilansetron or an acid addition salt can for example be mixed with the auxiliaries and/or carriers in a conventional manner and can be wet or dry granulated. The granules or powder can be poured directly into capsules or be pressed into tablet cores in a conventional manner. These can be coated in a known manner if desired.

The following example is intended to explain the production of pharmaceutical preparations containing cilansetron hydrochloride.

| Composition: | |
|---|---|
| Cilansetron hydrochloride monohydrate | 4 parts |
| Corn starch | 30 parts |
| Lactose | 70 parts |
| Kollidon 25 ™ | 5 parts |
| Magnesium stearate | 2 parts |
| Talcum | 3 parts |
| Total: | 114 parts |

Preparation Procedure

The active substance was mixed with corn starch and finely-powdered lactose in a mixer. The resulting mixture was moistened thoroughly with a 20% solution of polyvinylpyrrolidone (Kollidon 25$^{TM}$ by BASF) in demineralized water. If necessary, further demineralized water was added. The moist granules were passed through a 2 mm sieve, dried on trays at 40° C. and then passed through a 1 mm sieve (Frewitt machine). After mixing the granules with magnesium stearate and talcum, tablets of a weight of 114 mg were pressed therefrom, so that each tablet contained 4 mg of active substance.

Likewise, other pharmaceutical preparations of cilansetron, for example those known from EP 895,782 A2, may be used.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method at inhibiting irritable bowel syndrome (=IBS) in a non-obstipative male patient, said method comprising administering to said patient a pharmaceutical composition comprising an effective IBS inhibiting amount of cilansetron or a pharmacologically acceptable acid addition salt thereof or a solvate thereof.

2. A method according to claim 1, wherein said pharmaceutical composition comprises cilansetron hydrochloride.

3. A method according to claim 1, wherein said pharmaceutical composition comprises cilansetron hydrochloride monohydrate.

* * * * *

Disclaimer 6,566,369—Werner L. M. Cautreels, Weesp (NL); Claus Rudolf Steinborn, Seelze (DE); Heinz Guenter Krause, Burgdorf (DE); Steven David Caras, Marietta, GA; Egbertus Hendrikus Evert Biesheuvel, Weesp (NL); Albertus Hermannus Dirk Plekkenpol, Hilversum (NJ). MEDICAMENT CONTAINING CILANSETRON FOR THE TREATMENT OF NON-OBSTIPATIVE MALE IRRITABLE BOWEL SYNDROME PATIENTS. Patent dated May 20, 2003. Disclaimer filed December 30, 2003, by assignee, Sovay Pharmaceuticals GmbH.

Hereby enter this disclaimer to claims 1-3 of said patent.

*(Official Gazette, June 15, 2004)*